(12) United States Patent
Yokhin et al.

(10) Patent No.: US 6,947,520 B2
(45) Date of Patent: Sep. 20, 2005

(54) BEAM CENTERING AND ANGLE CALIBRATION FOR X-RAY REFLECTOMETRY

(75) Inventors: Boris Yokhin, Nazareth Illit (IL); Isaac Mazor, Haifa (IL); David Berman, Tivon (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 104 days.

(21) Appl. No.: 10/313,280

(22) Filed: Dec. 6, 2002

(65) Prior Publication Data

US 2004/0109531 A1 Jun. 10, 2004

(51) Int. Cl.$^7$ ............................................. G01N 23/20
(52) U.S. Cl. ........................... 378/70; 378/81; 378/207
(58) Field of Search ............................ 378/70, 81, 86, 378/205, 207

(56) References Cited

U.S. PATENT DOCUMENTS

| | | | |
|---|---|---|---|
| 4,725,963 A | 2/1988 | Taylor et al. ................. 704/40 |
| 5,151,588 A | 9/1992 | Kiri et al. ................. 250/208.1 |
| 5,574,284 A | 11/1996 | Farr ...................... 250/370.06 |
| 5,619,548 A | 4/1997 | Koppel | |
| 5,740,226 A | 4/1998 | Komiya et al. | |
| 5,923,720 A | 7/1999 | Barton et al. | |
| 5,949,847 A | 9/1999 | Terada et al. ................. 378/90 |
| 6,192,103 B1 | 2/2001 | Wormington et al. ......... 378/73 |
| 6,381,303 B1 | 4/2002 | Vu et al. ...................... 378/46 |
| 6,389,102 B2 | 5/2002 | Mazor et al. ................. 378/89 |
| 6,453,006 B1 | 9/2002 | Koppel et al. ................ 378/86 |
| 6,507,634 B1 | 1/2003 | Koppel et al. ................ 378/54 |
| 6,512,814 B2 | 1/2003 | Yokhin et al. | |
| 6,643,354 B2 | 11/2003 | Koppel et al. ................ 378/86 |
| 6,711,232 B1 | 3/2004 | Janik ........................... 378/70 |
| 6,744,850 B2 | 6/2004 | Fanton et al. ................. 378/83 |
| 6,744,950 B2 | 6/2004 | Alcksoff ...................... 385/48 |
| 6,771,735 B2 | 8/2004 | Janik et al. .................... 378/70 |
| 2001/0028699 A1 | 10/2001 | Iwasaki | |
| 2001/0043668 A1 | 11/2001 | Hayashi et al. | |
| 2002/0097837 A1 | 7/2002 | Fanton et al. | |
| 2002/0110218 A1 | 8/2002 | Koppel et al. | |
| 2003/0157559 A1 | 8/2003 | Omote et al. | |
| 2004/0052330 A1 | 3/2004 | Koppel et al. ................ 378/46 |

OTHER PUBLICATIONS

U.S. Appl. No. 10/078,640, filed Feb. 19, 2002, "Dual–Wavelength X–Ray Reflectometry", Assignee, Jordan Valley Applied Radiation Ltd.

Wiener, G, et al., "Characterization of titanium nitride layers by grazing–emission X–ray fluorescence spectrometry", Applied Surface Science, 125, 1998, pp 129–136.

Holy, V., et al., "High–Resolution X–Ray Scattering from Thin Films and Multilayers", Springer Verlag, 1999, pp 18–21.

(Continued)

Primary Examiner—David V. Bruce
Assistant Examiner—Courtney Thomas
(74) Attorney, Agent, or Firm—Christie, Parker and Hale, LLP (57) ABSTRACT

A method for testing a surface of a sample includes irradiating the surface at a grazing incidence with a beam of radiation having a focal region, whereby the radiation is reflected from the surface. At least one of the focal region and the sample is adjusted through a plurality of adjustment stages within an adjustment range so as to vary a location of the focal region relative to the surface. Respective angular profiles of the radiation reflected from the surface are measured at the plurality of adjustment stages, and the angular profiles are compared in order to select an adjustment within the range at which the surface is in a desired alignment with the beam.

42 Claims, 2 Drawing Sheets

OTHER PUBLICATIONS

A. Naudon et al., "New Apparatus for Grazing X-Ray Reflectometry in the Angle-Resolved Dispersive Mode", Journal of Applied Crystallography 22 (1989), p. 460–464

OXFORD Oxford Instruments Inc. X-Ray Technology Group, Scotts Valley, California, Series 5000/75 Packaged X-Ray tubes, Model XTF5011, Jun. 1999 (2 pages).

X-Ray Doubly-Bent Focusing Crystal Optic Test Report, Produced by X-Ray Optical Systems Inc.,, of Albany, New York, Nov. 2000 (1 page).

Data Sheet; Multichannel Detector Head with BT-CCD for Device No. S7032-0908N, Produced by Hamamatsu, of Hamamatsu City, Japan May 2000 (3 pages).

J. Spear, "Speeding low-k integration-Metrology for Low-k Materials", Silknet Aliance, 2003 (18 pages).

J.R. Levine Parrill, et al. "GISAXS-Glancing Incidence Small Angle X-ray Scattering", Journal de Physique IV 3 (Dec. 1993), pp. 411–417.

Jaklevic, et al., "High Rate X-Ray Fluorescence Analysis by Pulsed Excitation", IEEE Transactions on Nuclear Science NS-19:3 (1972), pp. 392–395.

Jaklevic, et al., "Small X-Ray Tubes for Energy Dispersive Analysis Using Semiconductor Spectrometers", Advances in X-Ray Analysis 15 (1972), pp. 266–275.

Jaklevic, et al., "Energy Dispersive X-Ray Fluorescence Spectrometry using Pulsed X-Ray Excitation", Advances in X-Ray Analysis 19 (1976), pp. 253–265.

Wormington, Characterization of Pore Size Distribution in Low k Dielectrics Using X-ray Reflectivity, presented at the Sematech Gate Stack Engineering Workshop (Austin, Texas, May 2, 2002) (17 pages).

Y. Ito et al, "X-ray Scattering Method for Determining Pore-Size Distribution in Low-k Thin Films", Presented at the International Sematech Ultra-Low-k Workshop (San Francisco, CA, Jun. 6–7, 2002) (22 pages).

N. Wu, et al., ":Substepping and its Application to HST Imaging", Astronomical Data analysis Software and Systems VII, ASP Conference Series, vol. 145, 1998; Jul. 28,–2003 (4 pages).

BEAM CENTERING AND ANGLE CALIBRATION FOR X-RAY REFLECTOMETRY

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Such measurements are particularly useful in evaluating layers deposited on semiconductor wafer substrates in the course of integrated circuit manufacture.

X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a detector mounted on a goniometer.

In order to obtain accurate measurements of film properties, it is necessary to precisely calibrate the angular scale of the reflection. Such a calibration requires, inter alia, exact control of the zero angle of reflection, so that the angle of the reflected beam relative to the surface can be determined accurately. (In the context of the present patent application and in the claims, the term "zero angle" refers to the orientation of a tangent to the reflecting surface at the point of incidence of the radiation.) To make reflectometric measurements with optimal accuracy, the zero angle at the measurement point should be known to within 0.005° or less. In classical reflectometers, a precision alignment procedure is used to calibrate the zero angle, as described by Holy et al., in *High-Resolution X-ray Scattering from Thin Films and Multilayers* (Springer Verlag, 1999), pages 18–21, which is incorporated herein by reference. The procedure involves aligning the surface of the sample vertically (i.e., along an axis perpendicular to the surface) with the irradiating X-ray beam, and adjusting the tilt angle of the surface relative to the goniometer scale.

Recently, fast X-ray reflectometers have been developed using position-sensitive detectors, such as a proportional counter or an array detector, typically a photodiode array or charge-coupled device (CCD). For example, U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

U.S. Pat. No. 5,740,226, to Komiya et al., describes a method for analyzing X-ray reflectometric data to determine film thickness. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

SUMMARY OF THE INVENTION

It is an object of some aspects of the present invention to provide improved methods and systems for X-ray reflectometry.

It is a further object of some aspects of the present invention to provide methods and systems for rapid, accurate alignment of a surface with a radiation source and detector that are to be used in testing the surface.

It is yet a further object of some aspects of the present invention to provide improved methods and devices for determination of the zero angle of a surface under reflectometric inspection.

In preferred embodiments of the present invention, a system for X-ray reflectometry comprises an X-ray source, which irradiates the surface of a sample under test at a range of angles near grazing incidence. An array of detectors captures the X-rays that are reflected from the surface. The sample is translated in a direction perpendicular to its surface in order to align the surface with the irradiating X-ray beam. Preferably, the X-ray source comprises optics for focusing the X-ray beam, and the position of the sample is adjusted so that the beam is focused on the surface, i.e., so that the beam incident on the surface at the point at which the beam has its narrowest width. Alternatively, the sample may be held stationary, and the X-ray source may be translated or otherwise adjusted.

To determine when the surface is properly aligned with the beam, the angular profile of the reflected X-rays is observed using the detector array. The inventors have observed that when the beam is properly focused on a flat surface, as described above, the reflection profile has a broad, flat peak region. This peak region corresponds to reflection from the sample over the range of angles between the zero angle (tangent to the surface) and the critical angle for total external reflection from the surface. As the system moves out of alignment, the flatness of the peak is distorted. By analyzing the shape of the profile as a function of sample position, the optimal alignment of the sample relative to the beam is determined rapidly, with high accuracy.

As noted above, the edges of the profile, to either side of the flat peak region, correspond to the zero angle and critical angle of the sample. The location of the first edge, at the low-angle end of the peak region, can thus be used to identify and calibrate the zero angle of the surface, relative to the detector array. This technique obviates the need to tilt the sample or move the detector in order to calibrate the zero angle, as in classical reflectometers. Once the zero angle is identified, the critical angle is determined precisely by the location of the second edge of the peak region.

Thus, in systems in accordance with the present invention, the radiation source and detector array are used to align samples quickly and conveniently, based on the angular profile of reflected radiation detected by the array. Although the preferred embodiments described herein are based on determining certain specific properties of the angular profile, other aspects of the profile may similarly be analyzed, alternatively or additionally, in order to carry out the calibration. Furthermore, although these preferred embodiments are directed particularly toward applications in X-ray reflectometry, the principles of the present invention may likewise be used for sample alignment in systems of other types. Such alternative methods and applications are considered to be within the scope of the present invention.

There is therefore provided, in accordance with a preferred embodiment of the present invention, a method for testing a surface of a sample, including:

irradiating the surface at a grazing incidence with a beam of radiation having a focal region, whereby the radiation is reflected from the surface;

adjusting at least one of the focal region and the sample through a plurality of adjustment stages within an adjustment range so as to vary a location of the focal region relative to the surface;

measuring respective angular profiles of the radiation reflected from the surface at the plurality of adjustment stages; and comparing the angular profiles in order to select an adjustment within the range at which the surface is in a desired alignment with the beam.

Preferably, comparing the angular profiles includes identifying a peak region in each of the profiles, and evaluating a shape criterion with respect to the peak region. Most preferably, evaluating the shape criterion includes assessing a flatness of the peak region, and wherein comparing the angular profiles includes selecting the adjustment at which the peak region is flattest. Additionally or alternatively, measuring the respective angular profiles includes measuring the reflected radiation over a scale of angles that includes a zero angle, tangent to the surface, and evaluating the shape criterion includes finding a first edge of the peak region in order to determine the zero angle. Further preferably, evaluating the shape criterion includes finding a second edge of the peak region in order to determine a critical angle for total external reflection from the surface.

There is also provided, in accordance with a preferred embodiment of the present invention, a method for testing a surface of a sample, including:

irradiating the surface at a grazing incidence with a converging beam of X-rays, whereby the X-rays are reflected from the surface;

adjusting a position of the sample through a range of positions in a direction perpendicular to the surface of the sample;

measuring respective angular profiles of the radiation reflected from the surface at a plurality of the positions within the range; and comparing the angular profiles in order to select a position within the range at which the surface is in a desired alignment with the beam.

Preferably, measuring the respective angular profiles includes measuring the reflected X-rays over a scale of angles that includes a zero angle, tangent to the surface. Most preferably, comparing the angular profiles includes selecting the position of the sample at which the surface substantially bisects a focal region of the converging beam of X-rays. In a preferred embodiment, irradiating the surface includes directing an X-ray source to irradiate the surface, and measuring the reflected radiation includes receiving the radiation using an array of detector elements, wherein at least one of the detector elements, in a vicinity of the zero angle with respect to the surface, receives a portion of the X-rays directly from the source, without reflection from the surface.

In a preferred embodiment, the method includes inducing a convexity in the surface of the sample while irradiating the surface.

In another preferred embodiment, the method includes translating the sample in a plane parallel to the surface so that the beam of X-rays is incident in sequence on a plurality of points on the surface, and repeating the steps of adjusting the position, and measuring and comparing the angular profiles so as to select the position at which the surface is in a desired alignment for each of the points.

There is additionally provided, in accordance with a preferred embodiment of the present invention, a method for testing a surface of a sample:

irradiating the surface with a beam of radiation over a range of angles at a grazing incidence with respect to the surface, whereby the radiation is reflected from the surface;

measuring an angular profile of the radiation reflected from the surface, the profile having a peak region bounded by first and second edges; and identifying a position of the first edge in the profile so as to determine an orientation of a tangent to the surface.

Preferably, the method includes identifying a second edge of the peak region in order to determine a critical angle for total external reflection from the surface, wherein the first and second edges are identified so as to define a full width at half maximum (FWHM) of the peak region.

Further preferably, irradiating the surface includes directing a converging beam of X-rays from an X-ray source toward the surface.

There is further provided, in accordance with a preferred embodiment of the present invention, apparatus for testing a surface of a sample, including:

a radiation source, which is adapted to irradiate the surface at a grazing incidence with a beam of radiation having a focal region, whereby the radiation is reflected from the surface;

an adjustment mechanism, which is adapted to adjust at least one of the focal region and the sample through a plurality of adjustment stages within an adjustment range so as to vary a location of the focal region relative to the surface;

a radiation detector, which is adapted to measure respective angular profiles of the radiation reflected from the surface at the plurality of adjustment stages; and a signal processor, which is adapted to compare the angular profiles in order to select an adjustment within the range at which the surface is in a desired alignment with the beam.

There is moreover provided, in accordance with a preferred embodiment of the present invention, apparatus for testing a surface of a sample, including:

an X-ray source, which is adapted to irradiate the surface at a grazing incidence with a converging beam of X-rays, whereby the X-rays are reflected from the surface;

a motion stage, which is adapted to adjust a position of the sample through a range of positions in a direction perpendicular to the surface of the sample;

a radiation detector, which is adapted to measure respective angular profiles of the radiation reflected from the surface at a plurality of the positions within the range; and a signal processor, which is adapted to compare the angular profiles in order to select a position within the range at which the surface is in a desired alignment with the beam.

Preferably, the radiation detector includes an array of detector elements, and at least one of the detector elements, in a vicinity of the zero angle with respect to the surface, receives a portion of the X-rays directly from the source, without reflection from the surface.

There is moreover provided, in accordance with a preferred embodiment of the present invention, apparatus for testing a surface of a sample:

a radiation source, which is adapted to irradiate the surface with a beam of radiation over a range of angles at a grazing incidence with respect to the surface, whereby the radiation is reflected from the surface;

a radiation detector, which is adapted to measure an angular profile of the radiation reflected from the surface, the profile having a peak region bounded by first and second edges; and a signal processor, which is adapted to identify a position of the first edge in the profile so as to determine an orientation of a tangent to the surface.

The present invention will be more fully understood from the following detailed description of the preferred embodiments thereof, taken together with the drawings in which:

DETAILED DESCRIPTION OF PREFERRED EMBODIMENTS

Figure 1:
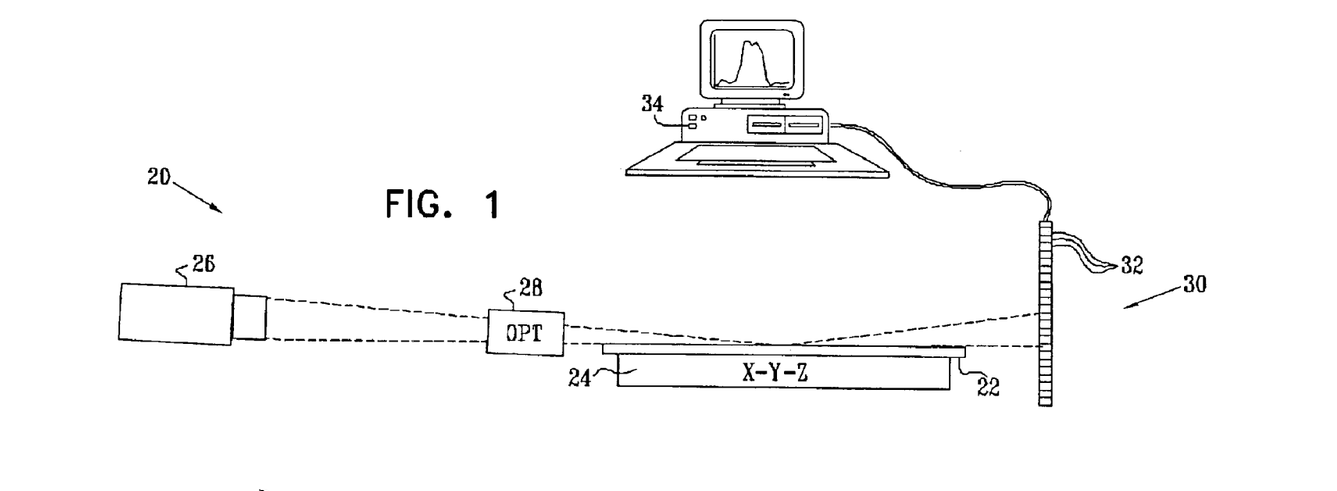
FIG. 1 is a schematic side view of a system for X-ray reflectometry, in accordance with a preferred embodiment of the present invention.

FIG. 1 is a schematic side view of a system 20 for X-ray reflectometry with enhanced alignment and calibration capabilities, in accordance with a preferred embodiment of the present invention. A sample 22, such as a semiconductor wafer, is securely placed on a motion stage 24, typically an X-Y-Z translation stage. (In the description that follows, the vertical direction in the figure, perpendicular to the surface of sample 22, is taken to be the Z-direction.) The sample is irradiated by an X-ray source 26, typically an X-ray tube. The X-ray beam output by source 26 is focused to a spot on the surface of sample 22 by suitable X-ray optics 28, preferably comprising a curved crystal monochromator, such as the Doubly-Bent Focusing Crystal Optic, produced by XOS Inc. (Albany, N.Y.). Other suitable optics are described in the above-mentioned U.S. Pat. Nos. 5,619,548 and 5,923,720, for example. Optics 28 may alternatively comprise cylindrical optics, which generate an elongated focal region on the sample.

X-rays reflected from sample 22 are received by an array 30 of detector elements 32, as is known in the art, typically a charge-coupled device (CCD) array, with silicon detector elements that are adapted for X-ray detection. Preferably, array 30 collects the reflected X-rays over a range of reflection angles between about 0° and 3°, relative to the sample surface. This range extends both below and above the critical angle of the sample for total external reflection. Although for simplicity of illustration, only a single row of detectors elements 32 is shown in FIG. 1, with a relatively small number of elements, array 30 generally includes a greater number of elements, arranged in either a linear or a matrix (two-dimensional) array. Further aspects of the implementation and operation of array 30 (along with other components of system 20) are described in U.S. patent application Ser. No. 09/833,902, filed Apr. 12, 2001, which is assigned to the assignee of the present patent application, and whose disclosure is incorporated herein by reference.

A signal processor 34 analyzes the output of array 30, so as to determine a distribution of the flux of X-ray photons reflected from sample 22 as a function of elevation angle $\phi$ at a given energy or over a range of energies. Processor 34 typically comprises a general-purpose computer with suitable input circuits for receiving the detector output, and software for analyzing the reflected radiation intensity, as described in the above-mentioned U.S. patent application Ser. No. 09/833,902. Typically, sample 22 has one or more thin surface layers, such as thin films, so that above the critical angle for total external reflection, the distribution of intensity as a function of elevation angle exhibits an oscillatory structure, due to interference effects among reflected X-ray waves from the interfaces between the layers. The oscillatory structure has a well-defined shoulder, corresponding to the critical angle, below which the reflectance of the surface is nearly 100%. Methods for measuring the critical angle (and an alternative method for determining the zero angle of a sample based on the critical angle) are described further in U.S. patent application Ser. No. 10/078,640, filed Feb. 19, 2002, which is assigned to the assignee of the present patent application, and whose disclosure is incorporated herein by reference.

Figure 2:
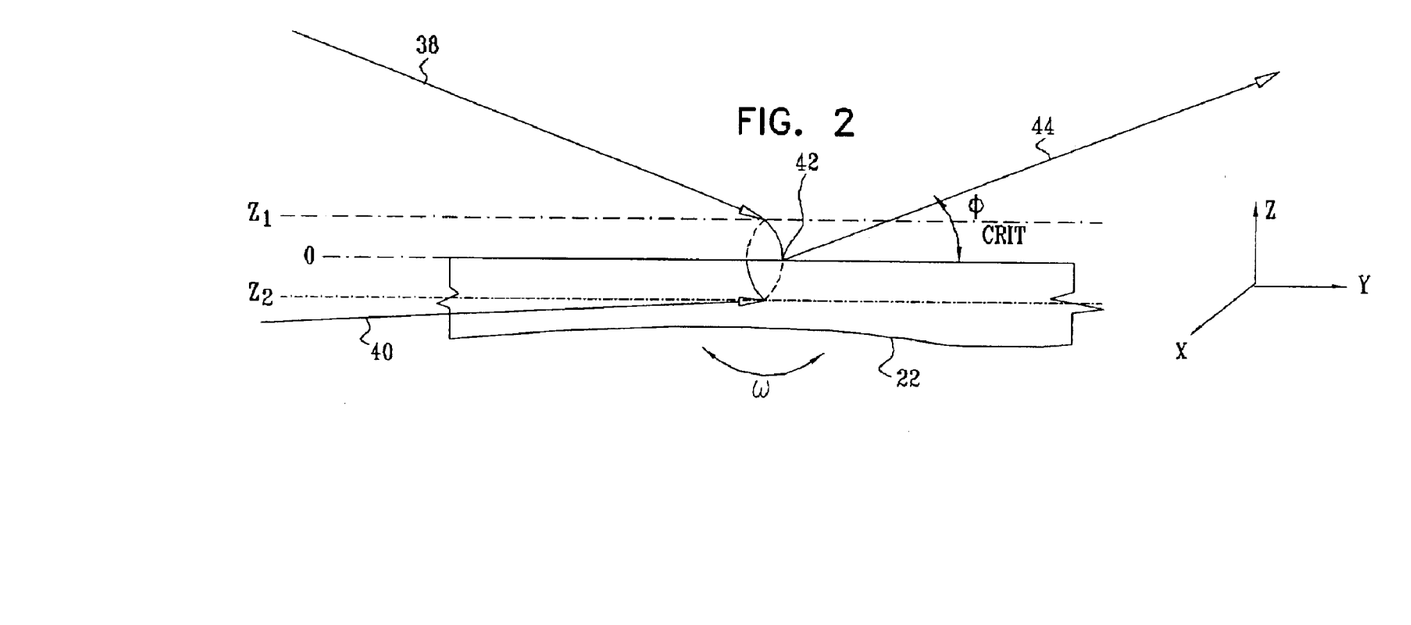
FIG. 2 is a schematic side view of a sample under X-ray irradiation in the system of FIG. 1.

FIG. 2 is a schematic side view of sample 22, showing details of the radiation incident on the sample and reflected therefrom. The radiation emitted by source 26 (FIG. 1) is focused by optics 28 into a converging cone, whose approximate edges are represented by arrows 38 and 40 in FIG. 2. Thus, X-rays are incident on the surface of sample 22 over a range of angles, between the upper limit represented by arrow 38 and the lower limit represented by arrow 40. Preferably, the tilt angle $\omega$ of sample 22 in system 20 is set so that the lower bound of the converging cone is slightly below the plane of the sample surface, as shown in the figure. This arrangement ensures that the zero angle of the surface is included within the cone. (Of course, radiation incident on the sample in the lower part of the incident beam, below the sample surface, is cut off at the side of the sample and is not actually incident on the surface.)

Optics 28 focus the cone of radiation to a focal waist 42. The waist is the point along the beam axis at which the beam has the smallest diameter, and beyond which the beam again diverges. Preferably, for accurate measurement by system 20, the beam is focused so that the diameter of waist 42 is as small as possible, typically about 40 $\mu$m. The Z-direction position of sample 22 is preferably adjusted by stage 22 so that the surface of the sample horizontally bisects waist 42, as shown in the figure. In other words, setting Z=0 as the Z-coordinate of the surface of the sample, and $Z_1$ and $Z_2$ as the upper and lower edges of the beam waist, respectively, the Z-position of the sample is adjusted so that $|Z_1|=|Z_2|$.

This position minimizes the size of the focal spot of the converging X-ray beam that is created on the surface of the sample. Minimizing the focal spot size on the sample surface is important for optimizing the spatial resolution of the measurements of system 20 with respect to the sample surface, and also enhances the angular precision of the reflectometric results.

X-rays are reflected from the sample surface over a range of angles corresponding to the range of the incident cone, i.e., between 0° and the upper limit angle represented by arrow 38. The critical angle $\phi_{crit}$ for total external reflection is represented in FIG. 2 by an arrow 44. (For clarity of illustration, the magnitude of the critical angle is greatly exaggerated in the figure. In reality, $\phi_{crit}$ is typically less than 1°.) As noted above, between 0° and $\phi_{crit}$, the surface of sample 22 reflects nearly 100% of the incident radiation. It will also be observed that a portion of the incident beam, angled roughly parallel to the sample surface between Z=0 and $Z=Z_1$, passes across the surface and impinges directly on the lower detectors in array 30 without having been reflected from the surface.

The analysis above assumes that the surface of the sample is flat, or at the least is not concave. A concave surface may cause a shadow in the X-ray beam, thus making accurate measurement of the X-rays near the zero angle difficult or impossible. Therefore, for samples that are liable to bend, such as semiconductor wafers, stage 24 is preferably configured to hold the sample so that the sample surface is flat to within very fine tolerance. The upper surface of the stage may even be slightly convex, in order to introduce a slight convexity in the upper surface of the sample. As the measurements of X-ray reflection from sample 22 described herein are local measurements, depending on the point of incidence of the X-ray beam on the sample, the measurements are not substantially affected by the convexity.

Figure 3:
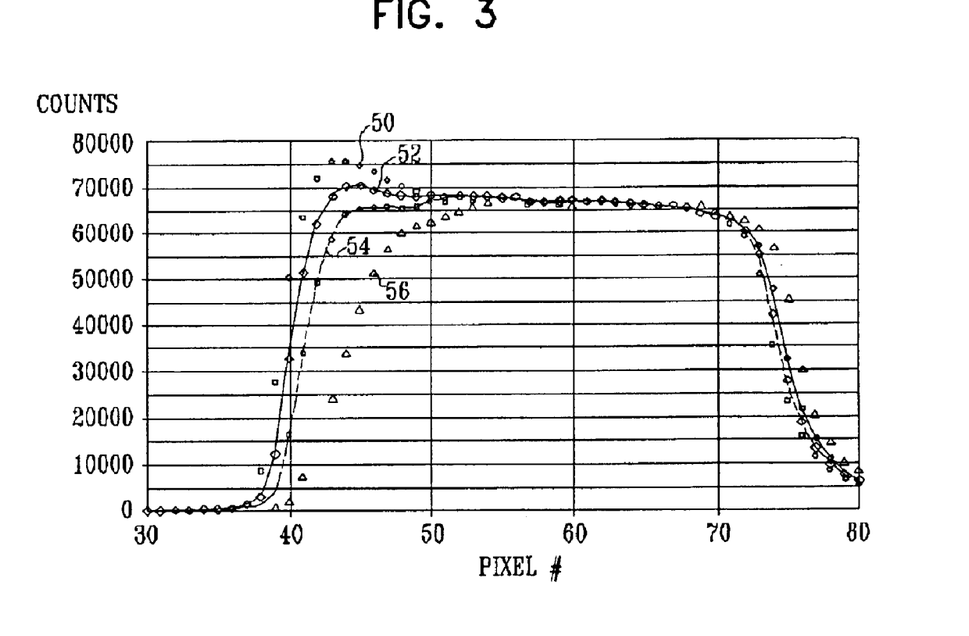
FIG. 3 is a schematic plot of angular profiles of X-rays reflected from a sample in the system of FIG. 1.

FIG. 3 is a schematic plot of measurement results obtained by processor 34 over a range of reflection angles from sample 22, at a number of different positions of the sample along the Z-axis. The sample in this case was a bare silicon wafer. The horizontal axis is marked in units of pixels, each pixel corresponding to one of detector elements 32 in array 30. In the present example, the pitch of the detector element was 24 µm, while the distance from the focal point of the X-ray beam (waist 42) to array 30 was 193 mm. Therefore, each pixel on the horizontal scale of FIG. 3 corresponds to about 0.00712° of elevation angle $\phi$.

Each measurement marked on the plot of FIG. 3 gives the number of counts (i.e., the number of X-ray photons) measured by the corresponding detector element 32 during a given measurement period. An upper trace 50 corresponds to the lowest position of the wafer (the largest value of $Z_1$, in the reference frame of FIG. 2), while a lower trace 56 corresponds to the highest position of the wafer, with traces 52 and 54 corresponding to two intermediate heights. The difference in the Z-position of the wafer from trace 50 to 52 was 5 µm, and similarly from trace 52 to 54, while the difference in Z-position from trace 54 to 56 was 10 µm.

Each of the traces shown in FIG. 3 has a broad, flat peak region, with a rising edge in the vicinity of pixels 40–45, and a falling edge at around pixel 75. The breadth of the peak region is about 0.25°. The rising edge corresponds to the zero angle for X-ray reflection, while the falling edge corresponds to the critical angle. In the vicinity of the rising edge, the photons incident on the detector elements also include a contribution from the zero-angle photons, which pass from optics 28 to array 30 directly, without reflecting from the sample at all. The lower the position of sample, the greater the contribution of these direct photons, leading to an elevated hump at the left side of the broad peak region in trace 50 and, less markedly, in trace 52. It can be shown based on geometric considerations that when $|Z_1|=|Z_2|$, the decreasing contribution of the direct photons as the elevation increases above the zero angle is exactly balanced by the increasing contribution of the reflected photons. Therefore, optimal Z-positioning of the sample should give the broadest, flattest peak region of the signal trace, somewhere between traces 52 and 54. When the sample is too high, the contribution of the direct photons is cut off, and the leading edge of the peak region is lower, as shown by trace 56.

Figure 4:
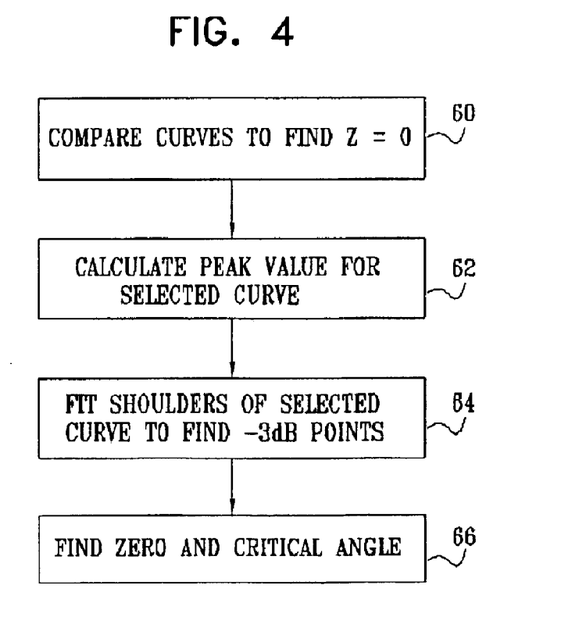
FIG. 4 is a flow chart that schematically illustrates a method for alignment and angular calibration of a sample in a system for X-ray reflectometry, in accordance with a preferred embodiment of the present invention.

FIG. 4 is a flow chart that schematically illustrates a method for aligning and calibrating the position and tilt angle of sample 22 in system 20, in accordance with a preferred embodiment of the present invention. Typically, system 20 is used to make reflectometric measurements on sample 22 at multiple different points on the sample surface. For this purpose, stage 24 preferably translates the sample in the X-Y plane, so that the X-ray beam is incident in turn on each of the points to be tested. The alignment and calibration procedure described below is most preferably carried out at each point individually, in order to avoid measurement errors due to fluctuations in the local height and tilt angle of the surface. It is an advantage of the present invention that this alignment and calibration procedure can be carried out quickly, typically in less than one second, so that repeating the procedure at each point does not significantly reduce the measurement throughput.

After system 20 has been coarsely aligned, using any suitable method known in the art, system 20 is operated to obtain traces of X-ray signal strength versus angle (or pixel number) for a number of different Z-positions of the sample, at a curve comparison step 60. The curves obtained at this step have the general form of the traces in FIG. 3. The number and spacing of the Z-coordinates of the sample in the different traces depends on the particular characteristics of system 20 and on the desired accuracy of alignment. The inventors have found that spacing the traces at Z-increments of 2 µm gives good results.

As explained above, the Z-position of the sample that gives the trace with the flattest peak region is identified as the optimal position, Z=0, for use in subsequent reflectometric analysis. "Flatness" is a heuristic term, and various criteria may be used to identify the flattest trace. One possible method is to take two adjoining ranges of pixels in the peak region of the traces, Range 1 and Range 2 (for example, pixels 46 to 55 and pixels 56 to 65 in FIG. 3), and to calculate $$\Delta = \sum_{Range1} C_j - \sum_{Range2} C_j,$$

wherein $C_j$ is the number of counts recorded by pixel j. The optimal Z-position for the sample is then found by plotting $\Delta$ against Z, and choosing the Z-position that gives $\Delta=0$. Alternative methods for finding the "flattest" trace will be apparent to those skilled in the art. Furthermore, other heuristic criteria, in addition to or instead of flatness, may be applied in order to select the Z-position at which to position sample 22 based on the traces collected at step 60.

Once the proper Z-adjustment is found, the trace that was collected closest to this Z-position is used to calibrate the zero angle of the sample. For this purpose, a peak value of the trace is calculated, preferably as an average over the peak region based on the sums used to find Δ, at a peak finding step 62. The peak value in this case is given by $$P = \frac{1}{N}\left(\sum_{Range1} C_j + \sum_{Range2} C_j\right),$$

wherein N is the number of pixels in the two ranges together. Then, on each of the leading and trailing edges of the peak regions, a point is found that is 50% (3 dB) lower than P, at a midpoint finding step 64. The distance between these midpoints is the full-width-half-maximum (FWHM) of the selected trace. To ensure that the 3 dB points are found accurately and consistently, polynomials are preferably fit to the count values of the pixels above and below the midpoints, typically five pixels on each side.

The fitting results on the leading and trailing edges of the trace are now used to identify the zero angle and the critical angle of sample 22, at an angle calibration step 66. The zero angle is the angle corresponding to the 3 dB point on the rising edge of the trace (as determined by the fitting procedure), while the critical angle is given by the 3 dB point on the falling edge. The angular span of each detector element 32 in array 30 is given by the pitch of the array divided by the distance from the focal point of the X-rays on the sample surface to the array. Since both these parameters are known, the critical angle can be determined simply by counting the number of detector elements between the 3 dB points on the chosen trace. Alternatively, other modes of analysis, based on curve fitting or other techniques, may be applied to the trace or traces found in step 60 in order to extract the zero angle and critical angle from the data.

In analyzing results of the type shown in FIG. 3, using the method of FIG. 4, the inventors were able to determine the critical angle for a sample silicon wafer ($\phi_{crit} \cong 0.227°$ for radiation on the Cu Kα1 line) to within about 0.006° of the theoretical value. This method can be carried out automatically, under the control of processor 34, in order to correct the Z-position of sample 22 and to calibrate the zero angle of a sample in less than one second. Once the initial, coarse adjustment of system 20 has been completed, no further tilt adjustment of the sample or the X-ray source is required. Whereas the method described above uses vertical motion of stage 24 to adjust system 20, a similar adjustment may be carried out by observing and analyzing the signal generated by array 30 while shifting X-ray source 26 and/or optics 28 so as to find the desired position of the X-ray focus on the sample surface.

Although system 20, as shown in FIG. 1, is configured for X-ray reflectometry, it will be appreciated that the methods of the present invention may similarly be used, mutatis mutandis, in other fields of X-ray analysis. Possible fields of application include X-ray fluorescence (XRF) analysis, and particularly grazing emission XRF, as well as other XRF techniques known in the art. Grazing emission XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. Furthermore, the principles of the present invention may be implemented in position-sensitive detection systems for other energy ranges, such as for detection of gamma rays and other nuclear radiation.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for testing a surface of a sample, comprising:
   irradiating the surface at a grazing incidence with a beam of radiation having a focal region, whereby the radiation is reflected from the surface;
   adjusting at least one of the focal region and the sample through a plurality of adjustment stages within an adjustment range so as to vary a location of the focal region relative to the surface;
   measuring respective angular profiles of the radiation reflected from the surface at the plurality of adjustment stages; and
   comparing the angular profiles in order to select an adjustment within the range at which the surface is in a desired alignment with the beam.

2. A method according to claim 1, wherein comparing the angular profiles comprises identifying a peak region in each of the profiles, and evaluating a shape criterion with respect to the peak region.

3. A method according to claim 2, wherein evaluating the shape criterion comprises assessing a flatness of the peak region, and wherein comparing the angular profiles comprises selecting the adjustment at which the peak region is flattest.

4. A method according to claim 2, wherein measuring the respective angular profiles comprises measuring the reflected radiation over a scale of angles that includes a zero angle, tangent to the surface, and wherein evaluating the shape criterion comprises finding a first edge of the peak region in order to determine the zero angle.

5. A method according to claim 4, wherein evaluating the shape criterion further comprises finding a second edge of the peak region in order to determine a critical angle for total external reflection from the surface.

6. A method according to claim 1, wherein adjusting at least one of the focal region and the sample comprises adjusting a position of the sample in a direction perpendicular to the surface of the sample.

7. A method for testing a surface of a sample, comprising:
   irradiating the surface at a grazing incidence with a converging beam of X-rays, whereby the X-rays are reflected from the surface;
   adjusting a position of the sample through a range of positions in a direction perpendicular to the surface of the sample;
   measuring respective angular profiles of the radiation reflected from the surface at a plurality of the positions within the range; and
   comparing the angular profiles in order to select a position within the range at which the surface is in a desired alignment with the beam.

8. A method according to claim 7, wherein comparing the profiles comprises identifying a peak region in each of the profiles, and evaluating a shape criterion with respect to the peak region.

9. A method according to claim 8, wherein evaluating the shape criterion comprises assessing a flatness of the peak region, and wherein comparing the angular profiles comprises selecting the adjustment at which the peak region is flattest.

10. A method according to claim 8, wherein measuring the respective angular profiles comprises measuring the reflected X-rays over a scale of angles that includes a zero angle, tangent to the surface, and wherein evaluating the shape criterion comprises finding a first edge of the peak region in order to determine the zero angle.

11. A method according to claim 10, wherein evaluating the shape criterion further comprises finding a second edge of the peak region in order to determine a critical angle for total external reflection from the surface.

12. A method according to claim 7, wherein measuring the respective angular profiles comprises measuring the reflected X-rays over a scale of angles that includes a zero angle, tangent to the surface.

13. A method according to claim 12, wherein comparing the angular profiles comprises selecting the position of the sample at which the surface substantially bisects a focal region of the converging beam of X-rays.

14. A method according to claim 12, wherein irradiating the surface comprises directing an X-ray source to irradiate the surface, and wherein measuring the reflected radiation comprises receiving the radiation using an array of detector elements, and
wherein at least one of the detector elements, in a vicinity of the zero angle with respect to the surface, receives a portion of the X-rays directly from the source, without reflection from the surface.

15. A method according to claim 7, and comprising inducing a convexity in the surface of the sample while irradiating the surface.

16. A method according to claim 7, and comprising translating the sample in a plane parallel to the surface so that the beam of X-rays is incident in sequence on a plurality of points on the surface, and repeating the steps of adjusting the position, and measuring and comparing the angular profiles so as to select the position at which the surface is in a desired alignment for each of the points.

17. A method for testing a surface of a sample:
irradiating the surface with a beam of radiation over a range of angles at a grazing incidence with respect to the surface, whereby the radiation is reflected from the surface;
measuring an angular profile of the radiation reflected from the surface, the profile having a peak region bounded by first and second edges; and
identifying a position of the first edge in the profile so as to determine an orientation of a tangent to the surface.

18. A method according to claim 17, and comprising identifying a second edge of the peak region in order to determine a critical angle for total external reflection from the surface.

19. A method according to claim 18, wherein the first and second edges are identified so as to define a full width at half maximum (FWHM) of the peak region.

20. A method according to claim 17, wherein irradiating the surface comprises directing a converging beam of X-rays toward the surface.

21. A method according to claim 20, wherein directing the converging beam comprises directing an X-ray source to irradiate the surface, and wherein measuring the angular profile comprises receiving the radiation using an array of detector elements, and wherein at least one of the detector elements, in a vicinity of the tangent to the surface, receives a portion of the X-rays directly from the source, without reflection from the surface.

22. Apparatus for testing a surface of a sample, comprising:
a radiation source, which is adapted to irradiate the surface at a grazing incidence with a beam of radiation having a focal region, whereby the radiation is reflected from the surface;
an adjustment mechanism, which is adapted to adjust at least one of the focal region and the sample through a plurality of adjustment stages within an adjustment range so as to vary a location of the focal region relative to the surface;
a radiation detector, which is adapted to measure respective angular profiles of the radiation reflected from the surface at the plurality of adjustment stages; and
a signal processor, which is adapted to compare the angular profiles in order to select an adjustment within the range at which the surface is in a desired alignment with the beam.

23. Apparatus according to claim 22, wherein the signal processor is adapted to identify a peak region in each of the profiles, and to evaluate a shape criterion with respect to the peak region in order to select the adjustment at which the surface is in the desired alignment.

24. Apparatus according to claim 23, wherein the signal processor is adapted to assess a flatness of the peak region, and to select the adjustment at which the peak region is flattest.

25. Apparatus according to claim 23, wherein the radiation detector is adapted to measure the reflected radiation over a scale of angles that includes a zero angle, tangent to the surface, and wherein the signal processor is adapted to find a first edge of the peak region in order to determine the zero angle.

26. Apparatus according to claim 25, wherein the signal processor is further adapted to find a second edge of the peak region in order to determine a critical angle for total external reflection from the surface.

27. Apparatus according to claim 22, wherein the adjustment mechanism is adapted to adjust a position of the sample in a direction perpendicular to the surface of the sample.

28. Apparatus for testing a surface of a sample, comprising:
an X-ray source, which is adapted to irradiate the surface at a grazing incidence with a converging beam of X-rays, whereby the X-rays are reflected from the surface;
a motion stage, which is adapted to adjust a position of the sample through a range of positions in a direction perpendicular to the surface of the sample;
a radiation detector, which is adapted to measure respective angular profiles of the radiation reflected from the surface at a plurality of the positions within the range; and
a signal processor, which is adapted to compare the angular profiles in order to select a position within the range at which the surface is in a desired alignment with the beam.

29. Apparatus according to claim 28, wherein the signal processor is adapted to identify a peak region in each of the profiles, and to evaluate a shape criterion with respect to the peak region in order to select the position at which the surface is in the desired alignment.

30. Apparatus according to claim 29, wherein the signal processor is adapted to assess a flatness of the peak region, and to select the adjustment at which the peak region is flattest.

31. Apparatus according to claim 29, wherein the radiation detector is adapted to measure the reflected X-rays over a scale of angles that includes a zero angle, tangent to the surface, and wherein the signal processor is adapted to find a first edge of the peak region in order to determine the zero angle.

32. Apparatus according to claim 31, wherein the signal processor is further adapted to find a second edge of the peak region in order to determine a critical angle for total external reflection from the surface.

33. Apparatus according to claim 28, wherein the radiation detector is adapted to measure the reflected X-rays over a scale of angles that includes a zero angle, tangent to the surface.

34. Apparatus according to claim 33, wherein the signal processor is adapted to select the position of the sample at which the surface substantially bisects a focal region of the converging beam of X-rays.

35. Apparatus according to claim 33, wherein the radiation detector comprises an array of detector elements, and wherein at least one of the detector elements, in a vicinity of the zero angle with respect to the surface, receives a portion of the X-rays directly from the source, without reflection from the surface.

36. Apparatus according to claim 28, wherein the motion stage is coupled to hold the sample so as to induce a convexity in the surface of the sample.

37. Apparatus according to claim 28, wherein the motion stage is further adapted to translate the sample in a plane parallel to the surface so that the beam of X-rays is incident in sequence on a plurality of points on the surface, and wherein the signal processor is adapted to select the position within the range in the direction perpendicular to the surface at which the surface is in the desired alignment for each of the plurality of the points.

38. Apparatus for testing a surface of a sample:
a radiation source, which is adapted to irradiate the surface with a beam of radiation over a range of angles at a grazing incidence with respect to the surface, whereby the radiation is reflected from the surface;
a radiation detector, which is adapted to measure an angular profile of the radiation reflected from the surface, the profile having a peak region bounded by first and second edges; and
a signal processor, which is adapted to identify a position of the first edge in the profile so as to determine an orientation of a tangent to the surface.

39. Apparatus according to claim 38, wherein the signal processor is adapted to identify a second edge of the peak region in order to determine a critical angle for total external reflection from the surface.

40. Apparatus according to claim 39, wherein the first and second edges define a full width at half maximum (FWHM) of the peak region.

41. Apparatus according to claim 39, wherein the X-ray source is adapted to direct a converging beam of X-rays toward the surface.

42. Apparatus according to claim 41, wherein the radiation detector comprises an array of detector elements, and wherein at least one of the detector elements, in a vicinity of the tangent to the surface, receives a portion of the X-rays directly from the source, without reflection from the surface.

* * * * *